United States Patent
Johns et al.

(10) Patent No.: US 12,233,192 B2
(45) Date of Patent: Feb. 25, 2025

(54) CELL WASHING APPARATUS

(71) Applicant: Haemair Limited, Swansea (GB)

(72) Inventors: William Richard Johns, Swansea (GB); Ronald Kelvin Knight, Swansea (GB)

(73) Assignee: Haemair Limited, Swansea (GB)

( * ) Notice: Subject to any disclaimer, the term of this patent is extended or adjusted under 35 U.S.C. 154(b) by 760 days.

(21) Appl. No.: 17/298,928

(22) PCT Filed: Dec. 11, 2019

(86) PCT No.: PCT/GB2019/053497
§ 371 (c)(1),
(2) Date: Jun. 1, 2021

(87) PCT Pub. No.: WO2020/120954
PCT Pub. Date: Jun. 18, 2020

(65) Prior Publication Data
US 2022/0031924 A1    Feb. 3, 2022

(30) Foreign Application Priority Data

Dec. 12, 2018 (GB) .................................. 1820272

(51) Int. Cl.
*A61M 1/36* (2006.01)
*A61M 1/02* (2006.01)
(Continued)

(52) U.S. Cl.
CPC ........ *A61M 1/3692* (2014.02); *A61M 1/0281* (2013.01); *A61M 1/34* (2013.01);
(Continued)

(58) Field of Classification Search
None
See application file for complete search history.

(56) References Cited

U.S. PATENT DOCUMENTS 5,017,293 A * 5/1991 Radovich ............ A61M 1/3403
210/646
5,130,026 A * 7/1992 Biselli .................... C12M 41/26
95/266
(Continued)

FOREIGN PATENT DOCUMENTS

BE          895193 A     5/1983
CN          1723051 A    1/2006
(Continued)

OTHER PUBLICATIONS

Office Action, and translation thereof, from counterpart Chinese Application No. 201980082965.0 dated May 17, 2023, 25 pp.
(Continued)

*Primary Examiner* — Clare M Perrin
(74) *Attorney, Agent, or Firm* — Shumaker & Sieffert, P.A.

(57) ABSTRACT

A cell washing apparatus is provided to wash a cell-containing fluid. The apparatus is arranged to exchange one or more exchangeable entities from a cell-containing first fluid, and comprises, a first fluid conduit and a second fluid conduit, the second fluid conduit separated from the first fluid conduit by a semi-permeable membrane disposed therebetween; the first fluid conduit having a first fluid inlet and a first fluid outlet, the first fluid conduit arranged to transport the first fluid in a first direction between the first fluid inlet and the first fluid outlet; the second fluid conduit being arranged to house a second fluid; wherein the semi-permeable membrane comprises a plurality of pores arranged to permit transport of said one or more exchangeable entities from the first fluid to the second fluid; wherein the one or more exchangeable entities comprise free haemoglobin and/or blood plasma; and wherein the first fluid is whole blood isolated from a human body, or packed red blood cells. The cell washing apparatus of the present invention aims to solve
(Continued)

the problem of harmful species that accumulate in a cell-containing fluid (such as, for example, transfusion blood) during storage and other applications, in which it is desired to transfer red blood cells to a clean suspending liquid.

15 Claims, 5 Drawing Sheets

(51) Int. Cl.
   *A61M 1/34* (2006.01)
   *A61M 1/38* (2006.01)
   *A61M 1/16* (2006.01)

(52) U.S. Cl.
   CPC ........ *A61M 1/3496* (2013.01); *A61M 1/3635* (2014.02); *A61M 1/38* (2013.01); *A61M 1/029* (2013.01); *A61M 1/1672* (2014.02); *A61M 1/3612* (2014.02); *A61M 1/3623* (2022.05); *A61M 2202/0085* (2013.01); *A61M 2202/0415* (2013.01); *A61M 2202/0433* (2013.01); *A61M 2205/3334* (2013.01)

(56) References Cited

U.S. PATENT DOCUMENTS

| | | | |
|---|---|---|---|
| 5,879,320 A | 3/1999 | Cazenave | |
| 7,220,257 B1 | 5/2007 | Lafontaine | |
| 9,649,423 B2 | 5/2017 | Evans et al. | |
| 2002/0085951 A1* | 7/2002 | Gelfand | A61M 1/36 422/44 |
| 2004/0073177 A1 | 4/2004 | Hickle | |
| 2007/0250050 A1 | 10/2007 | LaFontaine | |
| 2013/0059339 A1 | 3/2013 | Karerangabo et al. | |
| 2015/0086969 A1* | 3/2015 | Evans | A61M 1/0281 435/2 |
| 2015/0133854 A1 | 5/2015 | Zhu et al. | |
| 2016/0263304 A1 | 9/2016 | Kopperschmidt | |
| 2018/0015419 A1 | 1/2018 | Johns et al. | |

FOREIGN PATENT DOCUMENTS

| | | | |
|---|---|---|---|
| CN | 103415329 A | 11/2013 | |
| CN | 103861161 A | 6/2014 | |
| CN | 204815042 U | 12/2015 | |
| EP | 0780133 A1 | 6/1997 | |
| EP | 1897570 A1 * | 3/2008 | ......... A61M 1/0281 |
| FR | 2345165 A1 | 10/1977 | |
| FR | 2734726 A1 | 12/1996 | |
| FR | 2743726 A1 | 12/1996 | |
| JP | 2012100853 A | 5/2012 | |
| WO | 2018204206 A | 11/2018 | |

OTHER PUBLICATIONS

First Examination Report from counterpart Indian Application No. 202117026036 dated Jan. 6, 2023, 6 pp.

International Search Report and Written Opinion dated Mar. 16, 2020 from counterpart International Application No. PCT/GB2019/053497, 14 pp.

Notice of Intent to Grant from counterpart CN Application No. 201980082965.0 dated Jan. 11, 2024, 11 pp.

Search Report from counterpart GB Application No. GB1820272.1 dated May 22, 2019, 2 pp.

Search Report from counterpart CN Application No. 201980082965.0 dated Dec. 26, 2023, 3 pp.

* cited by examiner

CELL WASHING APPARATUS

This application is a national stage application under 35 U.S.C. § 371 of PCT Application No. PCT/GB2019/053497, filed Dec. 11, 2019, which claims the benefit of Great Britain Application No. 1820272.1, filed Dec. 12, 2018. The entire contents of each of PCT Application No. PCT/GB2019/053497 and Great Britain Application No. 1820272.1 are incorporated herein by reference in their entireties.

FIELD OF THE INVENTION

The present invention relates to cell washing apparatuses, and in particular to cell washing apparatuses for exchange of contaminants from blood, packed cells and similar fluids containing cells.

BACKGROUND TO THE INVENTION

One well-established way of washing cells contained in a fluid, such as red blood cells in blood, is to employ a centrifuge.

In the case of red blood cells, the blood (or red blood cell concentrate) is centrifuged within a centrifuge tube and the red blood cells collect to form a pellet at the bottom of the tube. The supernatant liquid, containing undesired species, is aspirated or decanted. The red blood cells are then resuspended in clean liquid through agitation.

If the resultant diluted concentration of undesired species remains too high, the centrifugation, pelleting, aspiration and resuspension process is repeated, and may be repeated several times.

Cell washing is part of the process for preparing transfusion blood, and has a variety of other applications. For example, it is employed to treat blood for autologous transfusion and can be used to clean old blood prior to transfusion.

One major disadvantage of centrifugal cell washing is that it is a batch process and the centrifugation, aspiration and corresponding agitation during resuspension, causes some cell rupture. This cell rupture introduces species into the resuspension fluid that the cell-washing process seeks to remove. Thus, not only does it reduce the available intact red blood cells, it reduces the efficiency of the cell-washing process.

Centrifugal cell washing is also a multi-step process, with each step in the process providing additional opportunity for error, which may result in damage to, or a partial/complete loss of, cells.

Centrifugal cell washing is a batch process. Hence, the washed blood cannot be used until at least one batch cycle is complete and subsequently washed blood is available in multiples of the batch size. A number of applications, including transfusion blood processing, may require an arbitrary quantity of fluid for processing, and the blood may be required with a very short lead time. Centrifugal cell washing, then, presents a number of undesirable features: the batch nature of the process is inflexible; and it causes some damage to the red blood cells being washed.

Current cell washing techniques are also time-consuming, which makes them less-suitable for applications requiring quick or immediate turn around, such as, for example, blood transfusion.

It is therefore desirable to provide a cell washing apparatus and technique which overcomes the disadvantages of the currently available solutions.

SUMMARY OF THE INVENTION

In accordance with a first aspect of the present invention, there is provided a red blood cell washing apparatus arranged to exchange one or more exchangeable entities in a cell-containing first fluid, the apparatus comprising, a first fluid conduit and a second fluid conduit, the second fluid conduit being separated from the first fluid conduit by a semi-permeable membrane disposed therebetween; the first fluid conduit having a first fluid inlet and a first fluid outlet, the first fluid conduit arranged to transport the first fluid in a first direction between the first fluid inlet and the first fluid outlet; the second fluid conduit being arranged to house a second fluid; wherein the semi-permeable membrane comprises a plurality of pores arranged to permit transport of said one or more exchangeable entities from the first fluid to the second fluid; wherein the one or more exchangeable entities comprise free haemoglobin and/or blood plasma; and wherein the first fluid is whole blood isolated from a human body, or packed red blood cells.

In accordance with a second aspect of the present invention, there is provided a cell washing apparatus arranged to exchange one or more exchangeable entities in a cell-containing first fluid, the apparatus comprising,
  a first fluid conduit and a second fluid conduit, the second fluid conduit being separated from the first fluid conduit by a semi-permeable membrane disposed therebetween;
  the first fluid conduit having a first fluid inlet and a first fluid outlet, the first fluid conduit arranged to transport the first fluid in a first direction between the first fluid inlet and the first fluid outlet; the second fluid conduit being arranged to house a second fluid; wherein the semi-permeable membrane comprises a plurality of pores arranged to permit transport of said one or more exchangeable entities between the first fluid and the second fluid.

Preferably the one or more exchangeable entities comprises one or more contaminants. The term "contaminant" in the context of the present invention will be understood by the skilled addressee to mean any entity located within the first fluid, wherein removal of said entity from the first fluid is desired. Said "contaminants" may or may not be harmful to the cells suspended within the cell-containing first fluid. In preferable embodiments, the one or more contaminants comprises free-haemoglobin and/or blood plasma.

Preferably said one or more exchangeable entities are exchanged with a replacement entity present in the second fluid. Preferably said replacement entity is a beneficial species. Preferably said exchange is by counter-diffusion. The replacement entity may, in some embodiments, be water.

The semi-permeable membrane comprises a plurality of pores preferably arranged to permit counter-diffusion of the first fluid and second fluid, so that one or more exchangeable entities present within the first fluid transfer into the second fluid away from the red blood cells, and are exchanged with replacement entities present in the second fluid, thus essentially washing the cells. The first fluid may be blood plasma (which, with the suspended cells, constitutes whole blood) or a solution such as SAGM (saline-adenine-glucose-mannitol) as widely used in packed cells for blood transfusion. The second fluid may be SAGM, or other fluid not containing the one or more exchangeable entities. The exchangeable entities may include free haemoglobin and/or iron and/or potassium ions, and/or other contaminants that arise during storage or processing of transfusion blood. The one or more exchangeable entities may, in some embodiments, be blood plasma. In such embodiments, complete fluid transfer between the first fluid and the second fluid may occur, thus resulting in a suspension of said cells in said second fluid. In such an embodiment, the second fluid conduit may comprise an outlet providing a stream of blood plasma exiting the apparatus.

Preferably, the semi-permeable membrane is further arranged to transport one or more beneficial species from a "clean" second fluid to the first fluid. In such preferable embodiments, the second fluid is preferably "clean" and said transport preferably provides an improved cell-suspending first fluid. In the context of the present invention, the term "clean" will be understood by the skilled addressee to mean having a zero, or lower, concentration of said one or more exchangeable entities compared with the first fluid. Thus, the cells may in said embodiments become suspended in a cleaned and "enhanced" first fluid, said cleaned and enhanced first fluid comprising a greater concentration of beneficial species. The beneficial species may, for example, include glucose, adenine, mannitol, a salt, an amino acid, a fungicide or any other suitable species beneficial to cells which will be appreciated by the skilled reader. In embodiments wherein the beneficial species is an amino acid, a preferable amino acid may be an essential amino acid such as, for example, L-glutamine.

In an example embodiment wherein the present apparatus is used to wash packed cells suspended in SAGM (saline-adenine-glucose-mannitol; an example first fluid), the second fluid may be "clean" SAGM, so that contaminants within the cell-containing SAGM may pass from the first conduit to the second conduit down a concentration gradient. In said example embodiment, said contaminants may be replaced with uncontaminated SAGM transferring from the second fluid to the first fluid in a counter-diffusion process. It is also possible that the first fluid may be whole blood and second fluid may be SAGM. By arranging the relative flow rates of the fluids, preferably in counter-current flow, a first fluid fed to the first conduit of the apparatus as whole blood may exit the apparatus from the first fluid outlet as packed cells in SAGM. The term packed cells will be understood by the skilled reader in the context of the present invention as concentrated cells—that is, cells contained within a fluid in a greater concentration than that of whole blood.

Preferably the second fluid conduit comprises a second fluid inlet and a second fluid outlet, the second fluid conduit arranged to transport a second fluid in a second direction between the second fluid inlet and the second fluid outlet. In embodiments wherein the second fluid does not move, the volume of first fluid that can be treated is limited by the capacity of the stationary second fluid. Thus, as treatment of the first fluid continues, the concentration of the one or more exchangeable entities in the second fluid increases until there is insufficient concentration gradient to remove more exchangeable entities from the first fluid. Similarly, the concentration of desirable species in the second fluid decreases until there is insufficient concentration gradient to drive desirable species from the second fluid. In such example embodiments, a predetermined volume of second fluid is arranged to treat a predetermined volume of first fluid, and/or an unknown volume of first fluid for a predetermined duration. As such, the extent of exposure of the first fluid to a stationary second fluid may be controlled such that optimum removal of said one or more exchangeable entities is permitted.

Transfer of the one or more exchangeable entities from the cell-containing first fluid into the second fluid is preferably more effective if the second fluid moves.

Preferably the first direction and the second direction are diametrically opposed. Preferably, most effective transfer of said one or more exchangeable entities from the first fluid to the second fluid is achieved when the first direction and the second direction are substantially, or at least approximately, diametrically opposed (counter-current flow). The terms "substantially diametrically opposed" and "approximately diametrically opposed" will be understood by the skilled addressee to mean that the "counter-current flow" of the first fluid and the second fluid in preferable embodiments is not intended to be limited to "exactly diametrically opposed". As such, flows having a difference in direction of between 135° and 180° may be considered to be "approximately diametrically opposed" or in "counter-current flow". Similarly, flows between 0° and 45° may be considered to be in the same direction, or "co-current flow", and flows between 45° and 135° may be considered to be orthogonal to one another, or "cross-current flow". There may be embodiments in which the flow is co-current or cross-current, or in which either the first or the second fluid may be stationary. If the first fluid is stationary during the washing process, it must be drained from the device after cleaning. There may be embodiments in which it is desirable for the second fluid to be stationary; for example, where there is no immediately convenient feed or drain for the second fluid. In practice, it has been identified that for some applications a stationary second fluid (and a moving first fluid) exhibit advantages over a moving second fluid. Such advantages have been seen in, for example, small animal blood transfusion. In any case, by providing the second fluid (the extractant, which may in some embodiments be SAGM), in a rigid second fluid conduit (of fixed volume) and passing the first fluid (which may, in some embodiments, be blood or packed red blood cells) through the first conduit (bounded by one or more semi-permeable membranes, which may be of fixed volume), there will be no net flow of the second fluid into the first fluid, or of the first fluid into the second fluid. Thus, in most preferable embodiments the first fluid exits the first fluid outlet having exactly the same volumetric flow rate as that when the first fluid entered the first fluid inlet, but with fewer contaminants.

In an alternative embodiment, the first direction and the second direction are the same (co-current flow). Such co-current flow of the first fluid and the second fluid may be desirable to limit the extent of change of composition of the first fluid and/or the second fluid. Optionally, the flows may be cross-current when emphasis is given to ease of construction and, in other embodiments, the relative direction of flow may be changed.

Preferably transport of said one or more exchangeable entities from the first fluid to the second fluid is by way of simple diffusion. Preferably, the apparatus operates in balanced counter-diffusion whereby the outlet flow is the same as the inlet flow for the first fluid and outlet flow is equal to the inlet flow of the second fluid. In the context of the present invention, the term "simple diffusion" will be understood by the skilled addressee to mean diffusion of a substance down a concentration gradient. Optional embodiments will be appreciated wherein one of the first conduit or the second conduit comprises a higher pressure than the other, which preferably promotes diffusion of a species (of which diffusion is required) across the semi-permeable membrane, in one direction or the other. For example, if it is wished to increase the concentration of cells in a first fluid exiting a first fluid outlet relative to the concentration of cells entering through a first fluid inlet, the pressure of the first fluid might be higher than that of the second fluid. In such example embodiments, there would be a net flow of the liquid phase from the first fluid to the second fluid. Where the relative flow rates of the two fluids are controlled to achieve desired concentrations of cells, the pressures within the device preferably automatically adjust without separate control of the pressures. With sufficiently large transfer area and with controlled liquid flow rates in counter-current flow, it is possible for either or both fluids to exchange completely. Thus, the first fluid can become the second fluid and vice versa. This is preferable in examples wherein the one or more exchangeable entities comprises blood plasma, and wherein it is desired to remove said blood plasma from the first fluid and replace the blood plasma with a red blood cell packing medium.

In comparison with a centrifugation-based cell-washing process, the present invention preferably exchanges a contaminated cell-containing first fluid with an uncontaminated second fluid in one step instead of successively: removing the contaminated first fluid by decantation after separating it from the cells by centrifugation; and then resuspending the cells in the clean second fluid. The present invention also differs from a filtration-based cell-washing process which might be pictured as follows: the cell-containing first fluid is filtered with a filtering device having pores sufficiently fine to retain the cells; the cells are then taken from the filtering device and resuspended in clean fluid. A filtering operation is typically a two-step process which merely separates cells from a contaminated first fluid. The first fluid composition remains the same.

The present invention preferably solves the problem of harmful species that can accumulate in a cell-containing fluid over time (such as, for example, an accumulation of free haemoglobin in transfusion blood during storage).

Previous solutions have provided a means for transferring cells from a first contaminated fluid to a second clean fluid. Excessive handling involved in multi-step procedures, and particularly those procedures which involve "rough" handling of cells (such as resuspension following pelleting by centrifugation) can cause damage and rupture to cells within a cell-containing fluid. Such damage and rupture can cause the release of intracellular species which have harmful effects when exposed extracellularly.

Preferably the plurality of pores has a pore diameter, the pore diameter being selected from the range: 0.2 μm to 5.0 μm. Preferably the pore diameter is selected from the range: 0.2 μm to 2.0 μm, which is preferably optimal for treating blood or fluids containing red blood cells.

Mammalian erythrocytes (red blood cells) are a nuclear and have the shape of a biconcave disc, the disc having a diameter of typically 6 μm to 8 μm. The pore size in the semi-permeable membrane separating the first conduit and the second conduit should therefore be sufficiently small to retain the red blood cells within the first fluid and large enough to permit the diffusion of the species to be exchanged (the one or more exchangeable entities). The pore size of the semi-permeable membrane of the present invention is preferably chosen according to the specific application of the apparatus, and may be in the range 0.2 μm to 5.0 μm.

Preferably the second fluid conduit extends through the first fluid conduit or the first fluid conduit extends through the second fluid conduit. Preferably the first fluid conduit and/or the second fluid conduit comprise a plurality of fluid channels. In most preferable embodiments, the plurality of channels of the first conduit extend through the second conduit. In other preferable embodiments, the plurality of channels of the second conduit may extend through the first conduit. The term "extend through" in the context of the present invention will be understood to mean that at least a portion of one of the first or second conduit may be located within the other conduit, such that an exterior surface of the conduit is in immediate contact with the fluid contained within the other conduit. As an example, an embodiment will be appreciated wherein the first conduit comprises a plurality of channels extending through the second conduit, providing an immediate interface between the plurality of channels and the second fluid contained within the second conduit. In said example, the walls of the plurality of channels comprise the semi-permeable membrane such that passage of said one or more exchangeable entities from the first fluid contained within the plurality of channels into the second fluid is permitted. The plurality of channels preferably provides a high surface area of the semi-permeable membrane for optimum diffusion of said one or more exchangeable entities, and optionally one or more beneficial species in counter-diffusion as discussed.

Preferably the first fluid contains red blood cells, which are suspended in the first fluid. In some embodiments, the one or more exchangeable entities comprises at least one selected from the group: free haemoglobin; free haem; free iron; blood plasma; potassium ions; lactic acid. One anticipated application of the present invention is for washing red blood cells when the first fluid is whole blood, blood plasma or a solution such as SAGM, which is widely used to suspend red blood cells to make up packed cells for blood transfusion. In this application, contaminants may include free haemoglobin; free haem; free iron; and potassium ions. Other anticipated applications for the present invention may for example include removing blood plasma from whole blood to produce a packed red blood cell suspension. In such an example, the one or more exchangeable entities comprise blood plasma. Other anticipated applications for the present invention may for example include removing one or more exchangeable entities (which may be contaminants) from a fluid containing one of any number of biological cells utilised within in a cell-culture based laboratory setting for research or clinical purposes. Such cells are preferably mammalian and may include primary cells or cell lines. In such example embodiments, the one or more exchangeable entities may comprise lactic acid, an industrially-applicable metabolite or substance (such as a medicament or antibiotic), or any number of components of a harmful secretome of proteins and non-protein components, such as lipids, micro-RNA and messenger-RNA which will be appreciated by the informed reader. In such applications, a contaminant or exchangeable entity in the first fluid may be a valuable product extracted in the second fluid; for example, an antibiotic.

In an example desired application of the present apparatus, the preferable inlet composition of the second fluid preferably depends on a desired output composition of the first fluid. For example, in washing blood, it is desired to remove as much free haemoglobin as possible from the first fluid when the inlet concentration of haemoglobin in the second fluid should be zero. Similarly, the desired outlet concentration of potassium ions is close to the normal concentration in blood of between 3.5 mmol/litre and 5.0 mmol/litre. Levels of potassium ions above 5.5 mmol/litre may be toxic. Transfusion blood accumulates potassium during storage and concentrations in excess of 20.0 mmol/litre are not unusual. It is then desirable that the second fluid contains a sufficiently low concentration of potassium ions to ensure transfer from the first fluid to the second fluid, but not sufficient to reduce the blood potassium concentration to below 3.5 mmol/litre. For example, the inlet concentration of potassium in the second fluid may be 3.5 mmol/litre. Where it is desired to create, or maintain, a packed cell suspension in SAGM (sodium chloride; adenine; glucose; mannitol), the second fluid may be SAGM. There are a variety of alternatives to SAGM and these alternative solutions may be employed as required.

Preferably the second fluid is an aqueous solution having a lower concentration of said one or more exchangeable entities than the first fluid. Preferably the second fluid comprises a higher concentration of one or more beneficial species than the first fluid. Preferably the second fluid comprises SAGM. Any suitable second fluid will be appreciated by the skilled addressee, and may for example include a fresh, uncontaminated first fluid (without cells). In an example embodiment wherein the first fluid comprises cell culture media comprising cultured cells, the second fluid may be fresh culture media or phosphate-buffered saline. A potential benefit of including low concentrations of said one or more exchangeable entities (such as, for example, potassium ions) may be to prevent concentrations of said exchangeable entities in the first fluid from subceeding a "healthy" lower threshold concentration (e.g. potentially resulting in, in the case of potassium in blood, hypokalemia). The ability to include low concentrations of the exchangeable entities in the second fluid can mean that continuous close inspection of, and control of, the composition of the first fluid flowing through the apparatus is not required in the present invention. As such, in some such preferable embodiments, the present invention provides a self-contained cell washing apparatus which does not require constant monitoring or control, and is preferably quicker and simpler to operate and may succeed in deskilling the process of washing cells. For example, if the volume of second fluid exceeds the volume of first fluid to be treated by 4:1, any inlet concentration of potassium in the first fluid between 3.5 mmol/l and 20 mmol/l will result in an outlet first fluid between 3.5 mmol/l and 7 mmol/l which when diluted with the residual blood in the recipient of the transfusion will fall within a safe range.

Preferably both the first and second fluids are gravity fed.

Preferably the first fluid outlet and/or the second fluid outlet each comprise an aperture having a size, wherein the size may be freely adjusted by a user. Preferably said adjustment of the size of the first fluid outlet aperture or the second fluid outlet aperture adjusts the rate of flow of the first fluid and/or the second fluid respectively. Preferably said adjustment of the first fluid outlet aperture size is arranged to provide a desired concentration of cells within the first fluid exiting the first fluid outlet aperture.

Preferably the apparatus comprises at least one fluid pump, the at least one fluid pump arranged to pump the first fluid and/or the second fluid. Preferably the pump is a metering pump, said metering pump being arranged to provide a precise concentration of cells contained within the first fluid exiting the first fluid outlet. Preferably the metering pump is positioned on the inlet and outlet of the first fluid flow to ensure a precise outlet cell concentration. In such embodiments, the present apparatus may be used to provide a concentrated cell-containing first fluid at the first fluid outlet, having a higher concentration of cells than the first fluid provided at the first fluid inlet.

In some embodiments, the apparatus comprises a temperature control member arranged to adjust the temperature of the apparatus. Preferably the temperature is freely adjustable by a user. In embodiments comprising a temperature control member, the temperature control member is arranged to be controlled by a user in order to set a desired temperature of the apparatus. Preferably the temperature control member is arranged to apply said temperature to any portion of the apparatus arranged to make contact with said first fluid and/or said second fluid. Preferably the temperature control member is arranged to provide a temperature suitable to minimise deleterious effects of temperature on cells contained within the cell-containing first fluid.

In most applications, it will not be necessary to control a temperature of the present apparatus, and in many example embodiments, a simple solution with few to no auxiliary components (like temperature control mechanisms) is most preferable. Transfusion for anaemia, for example, will rarely require temperature control as a unit of blood is provided over 30 to 60 minutes, but if there is rapid blood loss the transfusion needs to be rapid and this may cause a drop in body temperature, requiring warming of the blood. In several embodiments, it may also be unnecessary to control flow rates accurately. For example, in washing transfusion blood at or near the point of transfusion, it may be suitable to provide a blood (first fluid) bag and a bag of second fluid, both at, or about, room temperature. Both fluids are then preferably drip-controlled through the cell washing apparatus. We note that, approaching an infinite flow rate of the second fluid relative to the first, the liquid composition in the first fluid will asymptotically approach that of the second fluid. It is then clear that providing the flow rate of the second fluid is sufficiently high, accurate control of flow rate is not necessary to achieve a desired composition of the first fluid. Accurate control of the inlet and outlet flow rates of both fluids is required when it is desired to produce a packed cell suspension having an accurately controlled concentration of red blood cells. Where temperature control is required, it may be sufficient to provide the second fluid at a desired temperature. The mass-exchanger of the cell washer then also serves as a heat exchanger so that, in counter-current flow, the first fluid exits at a temperature close to that of the second fluid.

The apparatus of the first or second aspect may be applied at any point in the blood collection, processing and application cycle. It may be applied at, or soon after, the point of donation to convert whole blood to packed cells. It may be applied as an alternative to, or in conjunction with, centrifugation during the processing of the blood. It may be applied at, or just prior to, the point of transfusion in order to remove toxic species that accumulate during storage. Where applied during processing, a series of such apparatuses may be used in series, which each employ a semi-permeable membrane, each having a different pore size, or a range of pore sizes, in order to separate specific desired blood products. For example, white blood cells are much larger than red blood cells (at 12.0 µm to 15.0 µm) and could be separated from red blood cells with a membrane of suitable pore size.

Preferably the blood inlet is not in contact with a human body. Preferably the blood outlet is not in contact with a human body. Preferable embodiments of the present invention are intended to work separately to a human body and preferably do not require direct transfer of a fluid to or from a human body to or from the present invention. Thereby, in preferable embodiments the first fluid inlet is in fluid communication with a first fluid storage device or a first fluid reservoir. In the preferable embodiments the first fluid outlet is in fluid communication with a first fluid storage device or first fluid reservoir. In most of such preferable embodiments, the first fluid inlet is in fluid communication with a different first fluid storage device or first fluid reservoir to that in fluid communication with the first fluid outlet. In embodiments wherein the first fluid is blood or packed red blood cells, the first fluid storage device or first fluid reservoir preferably comprise a blood bag. Other suitable first fluid storage devices or reservoirs will be appreciated and may depend on the first fluid used with the present invention.

In accordance with the first or second aspect, blood or a red blood cell-containing first fluid are passed over one side of a semi-permeable membrane (which may be in the form of hollow fibres or flat sheets) and a second fluid (which may be an extracting solution) passed over the other side. Undesirable species, such as free haemoglobin, diffuse through the membrane into the second fluid, and additional species contained within the second fluid may diffuse across the membrane into the blood stream.

The technology of the first aspect of the present invention is particularly focused on removing toxic species from transfusion blood, when the extracting solution may preferably be SAGM (Saline, Adenine, Glucose, Mannitol) as is widely used to suspend red blood cells. Counter-current flow may be employed to maximize transfer rates across the membrane. The pore size in the membrane is preferably large enough to facilitate the passage of free haemoglobin (and preferably other harmful molecules) but not of red blood cells.

In alternative embodiments, for example when the cell-containing first fluid is a cell culture media comprising cells, the second fluid may, for example be fresh cell culture media or phosphate-buffered saline (PBS).

In accordance with a third aspect of the present invention, there is provided a method of conditioning stored transfusion blood or stored packed red blood cells, the method comprising the steps of:
  i. providing an apparatus in accordance with the first or second aspect of the present invention;
  ii. inserting transfusion blood or packed red blood cells through the first fluid inlet and subsequently passing said inserted transfusion blood or packed red blood cells through the first fluid conduit; and simultaneously,
  iii. passing a second fluid through the second fluid inlet and subsequently through the second fluid conduit; and
  iv. retrieving the transfusion blood or packed red blood cells from the first fluid outlet, the retrieved transfusion blood or packed red blood cells comprising a lower concentration of free haemoglobin and other potential contaminants than present in the inserted transfusion blood or packed red blood cells.

In accordance with a fourth aspect of the present invention, there is provided a method of washing cells, the method comprising the steps of:
  i. providing an apparatus in accordance with the first or second aspect of the present invention;
  ii. inserting a cell-containing first fluid through the first fluid inlet and subsequently passing said inserted cell-containing first fluid through the first fluid conduit; and simultaneously,
  iii. passing a second fluid through the second fluid inlet and subsequently through the second fluid conduit; and
  iv. retrieving the cell-containing first fluid from the first fluid outlet, the retrieved cell-containing first fluid comprising a lower concentration of one or more exchangeable entities than present in the inserted cell-containing first fluid.

Preferably the method of the third or fourth aspects further comprises a step before or during steps ii and iii, the step comprising:
  controlling an inlet flow rate and/or an outlet flow rate of the first fluid and/or the second fluid each having an inlet flow and an outlet flow, such that the outlet flow may differ from the inlet flow.

The term "inlet flow" will be understood in the context of the present invention to mean the first or second fluid entering the device, preferably through a first or second fluid inlet. The term "outlet flow" will be understood to mean the first or second fluid leaving the device, preferably through a first or second fluid outlet. The term "differ" will be understood to mean a compositional difference, such as, for example: a different concentration of a species in the second fluid outlet flow compared to the second fluid inlet flow; or a different concentration of cells in the first fluid outlet flow compared to the first fluid inlet flow.

Said control preferably allows a user to provide a desired outlet concentration of cells in the first outlet fluid (first fluid outlet flow) or a desired concentration of said one or more exchangeable entities in the second outlet fluid (second fluid outlet flow). Thus, a lower outlet flow rate than inlet flow rate gives a higher concentration of cells/exchangeable entities and a higher outlet flow rate gives a lower cell/contaminant concentration. In some embodiments, the one or more exchangeable entities (which may be include one or more "contaminants") may comprise a desired species, such as an antibiotic, produced by the cells of the first fluid, and thus collection of said antibiotic from the second outlet fluid is therefore preferable in such embodiments.

In embodiments wherein the first fluid comprises whole blood, preferably the method of the third or fourth aspects further comprises an additional step before step ii or after step iv, the step comprising:
  removing white blood cells from the first fluid.

A white blood cell filtration device, or alternatively an apparatus of the first or second aspects of the present invention may preferably be used to perform removal of said white blood cells. In said apparatus of the first and second aspects, the plurality of pores may be sized to permit transport of red blood cells from the first fluid to the second fluid, while maintaining larger white blood cells in the first fluid. Such an apparatus may be linked directly to a second apparatus arranged to extract one or more exchangeable entities from the resulting white blood cell-free second fluid, forming the red blood cell-containing first fluid of the second apparatus.

The essence of the third and fourth aspects of the present invention are to provide a method of exchanging harmful materials in a cell-containing first fluid (which may, for example, comprise blood) using a membrane-based technique, rather than a centrifuge-based technique. The present method uses a membrane-based mass-exchange to remove undesirable species from the first fluid into the second fluid. The method may also be used to transfer desirable species from the second fluid into the first fluid during the exchange. The present method is preferably particularly useful in the removal of free haemoglobin from transfusion blood.

Free haemoglobin is toxic and accumulates in transfusion blood as it is stored. The present invention preferably also removes free haem which can loosely attach to haemoglobin. The simplicity of the present invention preferably allows treatment of transfusion blood shortly, or immediately, before transfusion thus allowing no time for further haemolysis or for infection of the transfusion blood.

Thermodynamics dictates that, when two miscible fluids come into contact, they mix and the resulting mixture has a uniform composition. This uniformity applies also to materials suspended or dissolved in the fluids. For example, blood is an aqueous mixture containing both dissolved and suspended species. Dissolved species include potassium ions and suspended species include red blood cells. When blood contacts another aqueous mixture the two fluids tend to mix resulting in a mixture of uniform composition. When the contact is via a semi-permeable membrane, those species small enough to pass through the membrane become uniformly mixed, whilst those species too large to pass through the membrane remain on one side of said membrane. Where the pores are large enough to permit diffusion of haemoglobin, said haemoglobin tends to diffuse through the membrane to achieve an equal concentration on both sides of the membrane. By flowing a second fluid initially having zero concentration of haemoglobin on one side of the membrane, the free haemoglobin (not retained within red blood cells) diffuses from blood on the first side of the membrane into the flowing second fluid. Said flow of the second fluid carries the haemoglobin away so that further haemoglobin diffuses across the membrane until said haemoglobin within the blood approaches zero concentration in the second fluid flowing along the second side of the membrane. Similarly, the concentrations of all other species having molecules sized to fit through pores within the membrane are also depleted from the blood. These flows can be moderated by an electrical charge if a charged species is retained on one side of the membrane, but these effects are not significant in hampering the diffusion of haemoglobin and other potentially harmful species. Where the second fluid contains species not present in, or present in lower concentration in, the blood, those species will transfer out of the second fluid and into the blood. In this way, it is possible to ensure that, for example, for SAGM-suspended packed-cell transfusion blood, the desired SAGM concentration is attained or maintained in the red cell suspension. The present invention operates most effectively with a counter-current flow of blood and second fluid. Blood (or first fluid) leaving the device is thus continuously exposed to "fresh" second fluid. In the case of a preferable embodiment comprising blood as the first fluid, the second fluid contains zero free haemoglobin concentration. A benefit of counter-current flow is preferably that the outlet flow of one fluid exchanges with the inlet flow of the other and, given a large enough device, has the same composition. The outlet flow of the second fluid may be continuously exposed to the inlet flow of blood which enables cell-free first fluid (which may be blood plasma) to be recovered from the second fluid outlet. The resulting plasma can be used as source of medically valuable products including coagulation factors, albumin solutions and immunoglobulins.

The present invention also preferably allows control of the concentration of cells in the first fluid (for example red blood cells in packed cell transfusion blood). By maintaining equal inlet and outlet first fluid flows, the cell concentration within the first fluid remains the same at the outlet as it was at the inlet. A lower outlet flow gives a higher cell concentration and a higher outlet flow a lower cell concentration. The first fluid inlet preferably comprises a first fluid inlet aperture arranged to permit flow of the first fluid therethrough and into the first fluid conduit. The second fluid inlet preferably comprises a second fluid inlet aperture arranged to permit flow of the second fluid therethrough and into the second fluid conduit. Preferably each of said apertures comprises a respective diameter. Inlet flow and outlet flow for each of the first fluid and the second fluid can preferably be controlled in the present invention by changing the first fluid inlet aperture diameter, the first fluid outlet aperture diameter, the second fluid inlet aperture diameter, and/or the second fluid outlet aperture diameter.

Embodiments will be appreciated wherein the first fluid conduit comprises a plurality of first fluid outlets, and wherein said plurality of first fluid outlets are arranged to split a population of cells contained within said first fluid into two or more separate populations of cells.

Preferably the cell washing apparatus of the present invention eliminates the requirement for conventional cell washing techniques, such as centrifugation for example, steps of which can be damaging to cells. Preferably the apparatus of the present invention may be used to wash cells (such as red blood cells contained within transfusion blood) in a way that considerably reduces the extent of cell rupture compared to more conventional techniques. In many cases, any resulting cell rupture would normally result in the releasing of undesirable species into a surrounding cell-containing fluid. The preferable reduction in cell rupture using the apparatus of the present invention therefore preferably reduces the release of said undesirable species into said cell-containing fluid. Continuing with the example of red blood cells contained in transfusion blood, such undesired species may, for example, comprise free haemoglobin. Studies have shown that free haemoglobin can result in deleterious effects. For example, it can make the patient more susceptible to disease and cause renal damage.

By comparison with more conventional techniques for cell washing, the present invention preferably provides a simpler solution, comprising fewer steps. Preferable embodiments of the present invention provide single-step real-time cell washing, rather than a cyclic such as that required for conventional batch techniques, such as centrifugation and resuspension.

Preferable embodiments of the present invention comprise no moving parts. Said preferable embodiments are thereby preferably optimally compact, and preferably therefore maximise space economy. Such embodiments are therefore preferably advantageous in applications wherein space is at a premium, and/or applications wherein moving parts and any resulting vibration would compromise any fragile or delicate techniques or procedures occurring within close proximity, such as on the same bench for example. Present techniques which include moving parts, such as centrifugation, often result in vibrations which can hinder techniques requiring little to no movement. Such techniques may for example include those requiring adhesion of cells, single-cell patch clamp, single-cell transfection, or other delicate techniques which will be apparent to the skilled addressee. Current solutions include accounting for such vibrations in lab design, such as by isolating a surface comprising a centrifuge from any surface upon which a delicate procedure is to be performed. In environments wherein space is at a premium however, such solutions are not possible.

In example embodiments wherein the present invention is used to wash red blood cells in transfusion blood, said embodiments preferably maximise space economy and provide the ability to perform cell washing adjacent to a patient and thereby eliminating any delay, present in conventional solutions, in transporting transfusion blood to be washed (for example by centrifugation), and transporting washed blood to a patient.

The present invention preferably provides an apparatus permitting cell washing using fewer steps, and most preferably provides single-step real-time cell washing. Such embodiments are advantageous for use alongside techniques and procedures wherein time is constrained. Examples of such time-constrained techniques may include multi-step protocols, wherein a cell washing step would ordinarily be the longest step in said protocol when using conventional techniques. Examples may also include time-critical blood transfusion events.

Preferable embodiments of the present invention provide a continuous flow of cell-containing fluid and can preferably wash an arbitrarily small or large volume of cell-containing fluid (for example a transfusion blood sample). By contrast, previously available technology typically places maximal or minimal limits on cell-containing fluid volume to be washed. In the case of centrifugation, the maximal volume is limited by the capacity and number of centrifuge chambers available. Minimal limits on the volume of fluid to be centrifuged are also placed by the requirement for generating a cell pellet to be resuspended.

Previous techniques of washing samples (such as blood samples), by centrifugation for example, often involves arbitrary volumes, which can present an additional issue/step of balancing said centrifuge. The present invention preferably overcomes the issues involved with this additional step of washing arbitrary volumes of cell-containing liquid.

Additional steps within previous cell washing techniques provide additional opportunities for cells or samples to be partially or completely lost, contaminated or damaged. The present invention preferably provides a simpler solution having a single continuous flow of a cell-containing fluid, rather than a series of operations, which in centrifugation would include alternately concentrating and resuspending the cells.

DETAILED DESCRIPTION

Specific embodiments will now be described by way of example only, and with reference to the accompanying drawings, in which.

Figure 1:
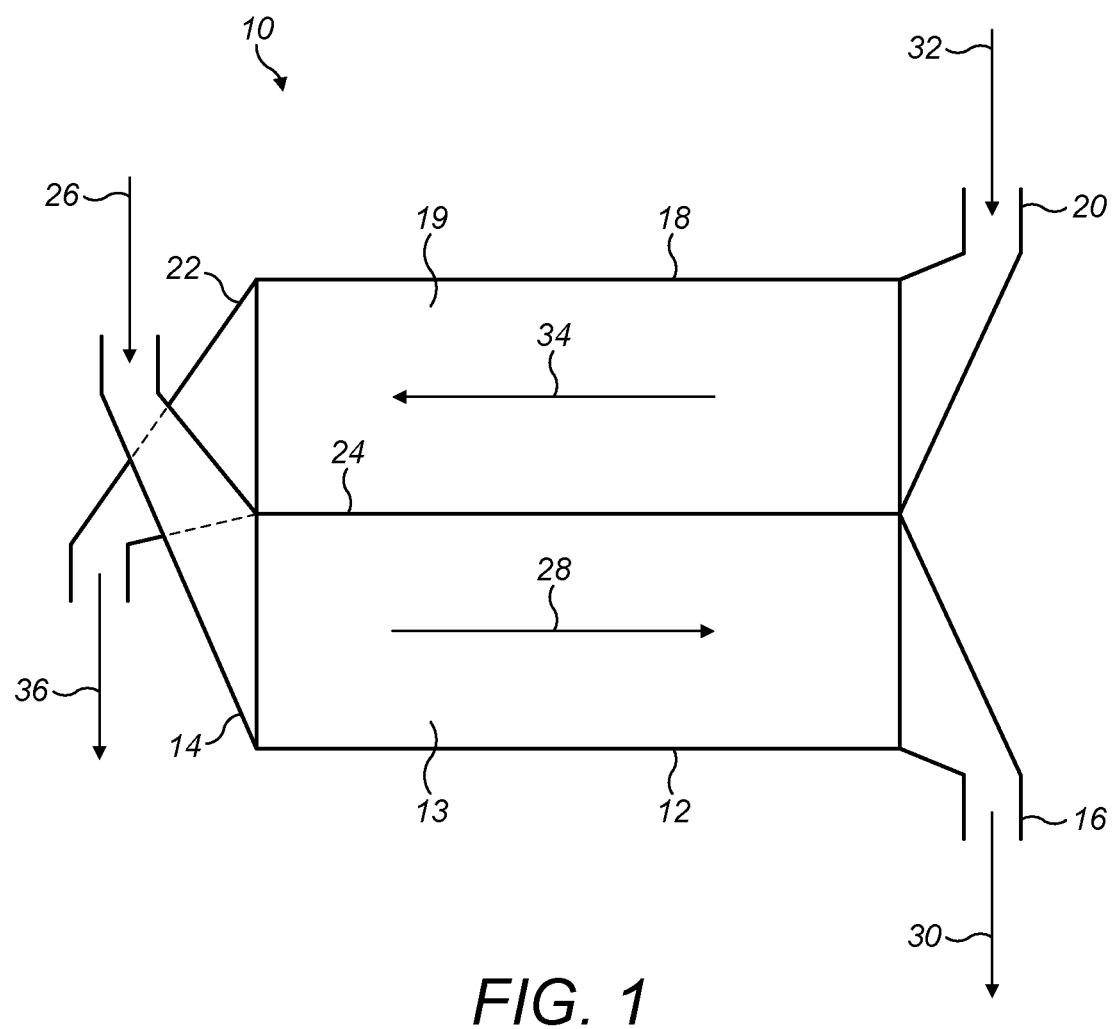
FIG. 1 shows a sectional view of an example cell washing apparatus in accordance with the first aspect or second of the present invention.

Referring to FIG. 1, a simple example embodiment of a cell washing apparatus 10 according to the first or second aspect of the present invention is shown. In the embodiment shown, the cell washing apparatus 10 comprises a substantially cuboidal first fluid conduit 12, forming a substantially planar sheet, having a longitudinal axis arranged in a horizontal orientation such that a first end of the first fluid conduit 12 is affixed to a first fluid inlet manifold 14 having a first fluid inlet aperture permitting inflow 26 of a cell-containing first fluid into a cavity 13 of the first fluid conduit 12. At a second end of the first fluid conduit 12 is affixed a first fluid outlet manifold 16 having a first fluid outlet aperture arranged to permit outflow 30 of the cell-containing first fluid from the cavity 13 of the first fluid conduit 12.

Positioned adjacent the first fluid conduit 12 and having the same orientation is a substantially cuboidal second fluid conduit 18, forming a second substantially planar sheet. The second fluid conduit 18 comprises a first end having affixed thereto a second fluid inlet manifold 20 comprising a second fluid inlet aperture arrange to permit inflow 32 of a second fluid into a cavity 19 of the second fluid conduit 18. At a second end of the second fluid conduit 18 and affixed thereto is a second fluid outlet manifold 22 having a second fluid outlet aperture arranged to permit outflow 36 of the second fluid from the cavity 19 of the second fluid conduit 18.

The apparatus 10 further comprises a semi-permeable membrane 24 positioned between the first fluid conduit cavity 13 and the second fluid conduit cavity 19 and providing a semipermeable interface therebetween. The semipermeable membrane 24 comprises a plurality of pores arranged to permit diffusion of substances between the first fluid conduit cavity 13 and the second fluid conduit cavity 19.

In use, the first fluid inlet manifold 14 is in fluid communication with a first fluid container (not shown) positioned above the apparatus 10 and oriented such that a cell-containing first fluid flows out of the first fluid container by force of gravity. The first fluid outlet manifold 16 is in fluid communication with a first fluid collection container (not shown) arranged to collect the cell-containing first fluid from the first fluid outlet manifold 16. Under force of gravity, the cell-containing first fluid exits the first fluid container 26 and flows in a horizontal first direction 28 through the first fluid conduit 12 and out 30 to the first fluid collection container. The first fluid collection container is positioned below the first fluid outlet manifold 16 to aid continued flow of the first fluid by force of gravity alone.

Further in use, the second fluid inlet manifold 20 is in fluid communication with a reservoir (not shown) of a second fluid, the reservoir positioned above the second fluid inlet manifold 20. Positioned between the reservoir and the second fluid inlet manifold 20 is a pump (not shown) arranged to pump the second fluid such that it flows from the reservoir 32 toward the second fluid inlet manifold 20. The second fluid subsequently passes in a horizontal second direction 34, diametrically opposed to the first direction 28, along the second fluid conduit 18 and out of the second fluid outlet manifold 22 to a waste container (not shown) 36, the waste container being positioned below the second fluid outlet manifold 22. In the embodiment shown, the second fluid may also travel from the second fluid reservoir, into and out of the apparatus by force of gravity alone.

The flow of the cell-containing first fluid 26, 28, 30 and the flow of the second fluid 32, 34, 36 occurs simultaneously. Transfer of species between the cell-containing first fluid and the second fluid occur by way of the semi-permeable membrane 24 during counterflow of the cell-containing first fluid and the second fluid. The cuboidal first conduit 12 and second conduit 18 are each in the form of substantially planar sheets providing a large surface area of contact between the first fluid conduit 12 and the second fluid conduit 18. In the embodiment shown, the entire surface of contact between the first fluid conduit 12 and the second fluid conduit 18 is comprised of the semi-permeable membrane 24.

In the embodiment shown, the cell-containing first fluid is stored transfusion blood containing red blood cells, which is stored in a blood bag. Handling and storage of the transfusion blood over time causes degradation of red blood cells, resulting in leaking of free haemoglobin into the surrounding blood. Said free haemoglobin has been implicated in post-transfusion morbidity. Accumulation of such toxic species over time is common not only in transfusion blood, but in any cell-containing fluid. Cells grown in laboratory culture generate toxic waste products which are required to be periodically "washed" from the surrounding cell culture medium.

In the example embodiment shown in FIG. 1, the blood bag is positioned above the apparatus 10 and oriented such that the blood flows downward toward the first fluid inlet manifold by force of gravity. The pores of the semi-permeable membrane 24 of the example shown are sized at a minimum of 0.2 µm to a maximum of 2.0 µm, and are therefore sized to permit passage of toxic metabolites and free haemoglobin from the first fluid to the second fluid, but also to prevent passage of red blood cells out of the first fluid across the membrane 24.

Figure 2:
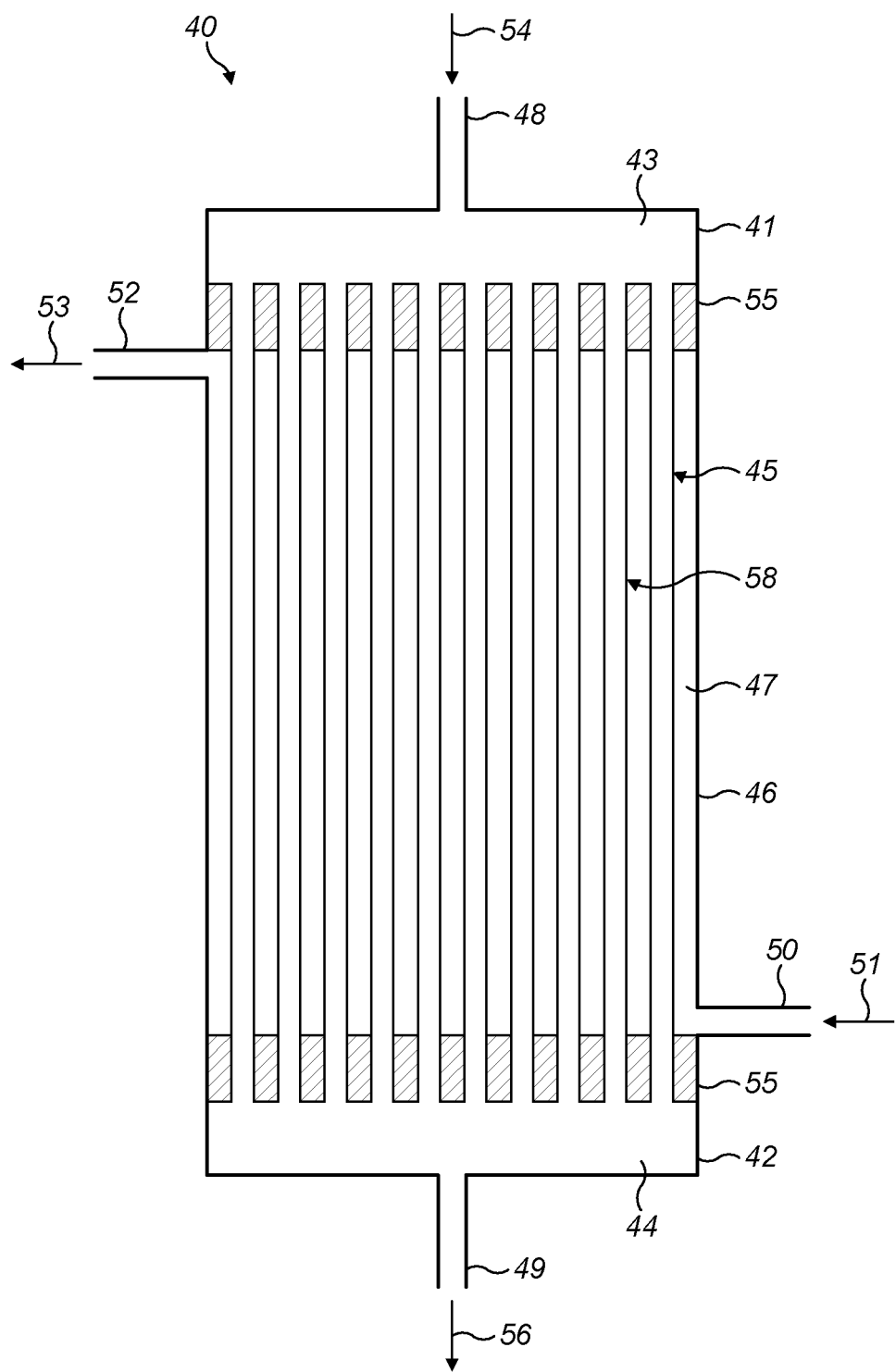
FIG. 2 shows a sectional view of a second example cell washing apparatus in accordance with the first or second aspect of the present invention.

A more complex example of a cell washing apparatus 40 of the first or second aspect of the present invention is shown in FIG. 2, which shows a substantially cylindrical elongate housing defining a first fluid conduit having an uppermost first entry portion 41 defining a first entry cavity 43, and a lowermost second exit portion 42 defining a second exit cavity 44, wherein each of the first entry cavity 43 and the second exit cavity 44 are in fluid communication by way of a plurality of elongate cylindrical channels 45. The elongate housing further comprises a second fluid conduit 46 positioned between the first entry cavity 43 and the second exit cavity 44 of the first fluid conduit. The plurality of channels 45 extend through a cavity 47 of the second fluid conduit 46, and wherein said channels 45 are secured within the second fluid conduit cavity 47 at either end thereof by potting 55.

Extending from the uppermost first entry cavity 43 of the first fluid conduit is a first fluid inlet 48, and extending from the lowermost second exit cavity 44 is a first fluid outlet 49. Extending from a lowermost portion of the second fluid conduit 46 is a second fluid inlet 50, and extending from an uppermost portion of the second fluid conduit 46 is a second fluid outlet 52. The second fluid outlet 52 is positioned above the second fluid inlet 50 each being oriented such that they are diametrically opposed. As such, in use, a second fluid such as that described hereinbefore is arranged to flow 51 into the second fluid conduit 46 by way of the second fluid inlet 50. Flow of the second fluid subsequently proceeds in an upwardly oriented direction toward the second fluid outlet 52. The first fluid flows into the first fluid inlet 48 and in a downward direction into the first fluid entry cavity 43, through the elongate channels 45, and toward the first fluid exit cavity 44 where the first fluid converges and exits 56 the first fluid conduit by way of the first fluid outlet 49.

In the embodiment shown, the elongate channels 45 comprise walls separating the elongate channels from the second fluid conduit 46, wherein the walls comprise a semi-permeable membrane comprising pores arranged to permit the diffusion of substances between the two fluids.

Figure 3:
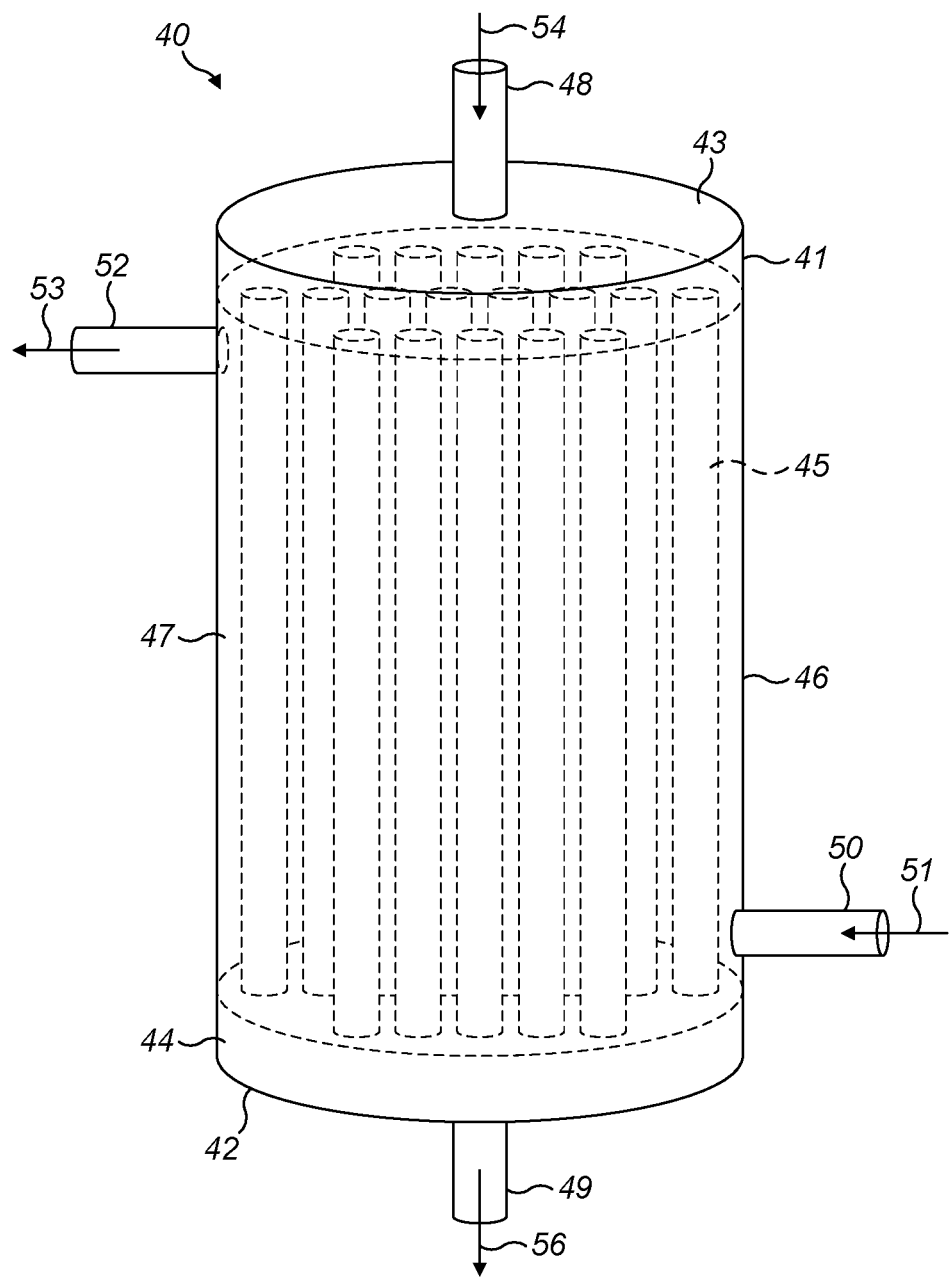
FIG. 3 shows a perspective view of the cell washing apparatus shown in FIG. 2.

FIG. 3 shows a perspective view of the apparatus described and shown in FIG. 2.

In the example embodiment shown in FIG. 2 and FIG. 3, the first fluid conduit comprises a plurality of channels 45 arranged to extend through the cavity 47 of the second fluid conduit 46. Alternate embodiments will be appreciated wherein the elongate channels are of rectangular cross-section, rather than the cylindrical channels shown, and embodiments wherein the inlet and outlet ports are shaped to give a more uniform distribution of the fluid between the channels. The cylindrical (hollow fibre) membranes may also be replaced by planar (flat sheet) membranes.

Figure 4:
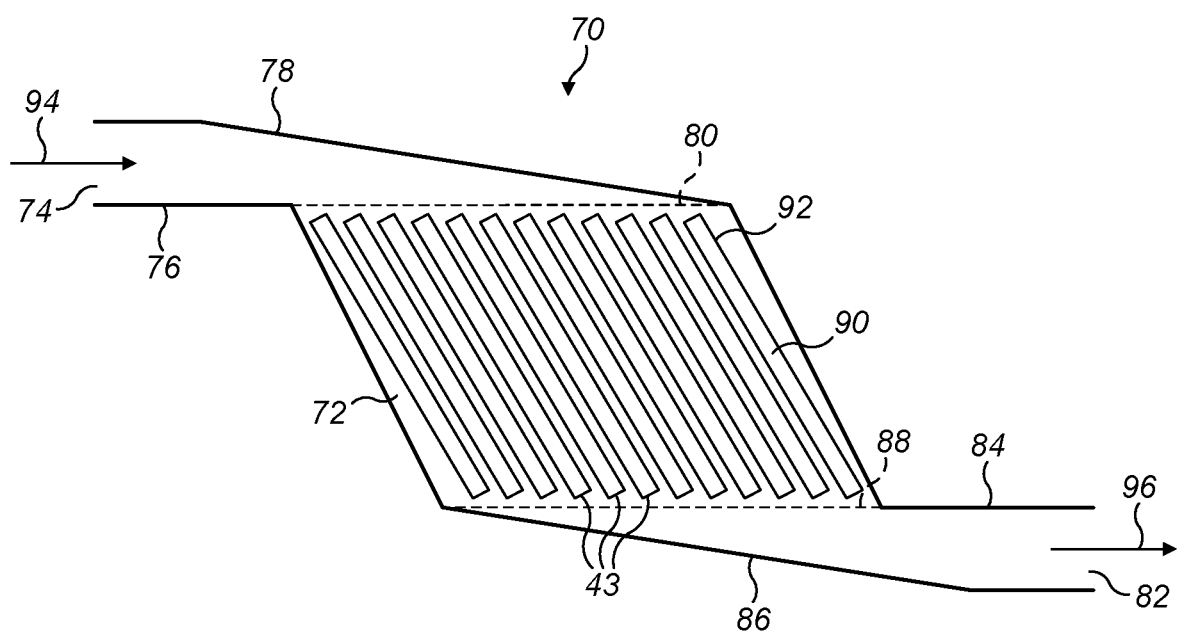
FIG. 4 shows a sectional view of a third example cell washing apparatus in accordance with the first or second aspect of the present invention.

FIG. 4, shows such an embodiment 70 which incorporates both flat sheet membranes and entry and exit ports designed to give a more uniform flow of the fluids between the channels. The illustration shows flat-sheet membranes wherein the second fluid conduit 90 is arranged to extend through the first fluid conduit 72. In the embodiment 70 of FIG. 4, the elongate channels 92 of the second fluid conduit 90 are formed of substantially planar sheets. The first fluid enters as stream 94 and flows into the narrowing headspace 74 to give a uniform flow between the channels 90. The fluid exits as stream 96 through broadening space 82 again to promote uniform flow distribution between the channels 90. The second fluid inlet and outlet ports distributing the fluid to flow within the channels 90 is not illustrated. In counter-current flow, the second fluid enters at the bottom of the device and exits at the top.

The embodiments described and shown are in a vertical orientation but the apparatus according to the present invention operates equally well at any orientation. In another manifestation, the apparatus could have a rectangular cross-section. In yet another manifestation, the first fluid could enter and leave by the sides of the entry and exit spaces and the spaces may be angled so that the velocity of the first fluid remains approximately constant as it flows across the top of the channels (so that the depth is zero opposite the first fluid entry and exit). Similarly, the space at the bottom may be angled so that the depth opposite the exit is zero.

Figure 5:
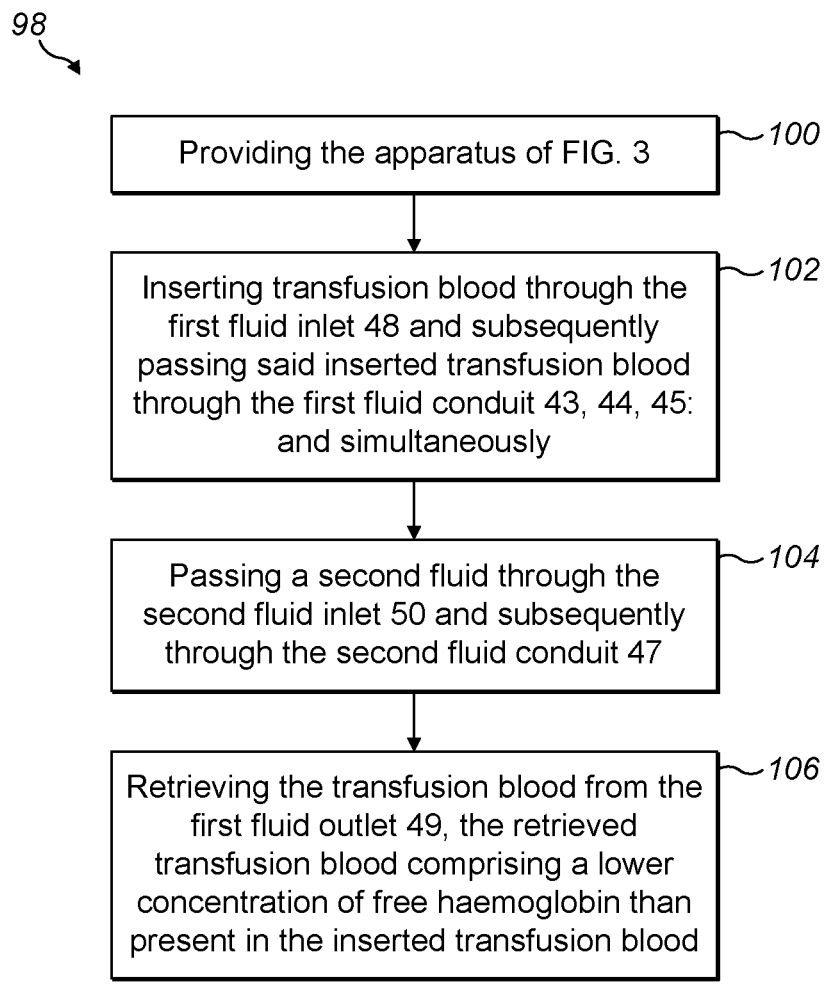
FIG. 5 shows an example embodiment of a method according to the third or fourth aspect using an apparatus as shown in FIG. 3.

FIG. 5 shows a method in accordance with the third or fourth aspects of the present invention, the method comprising the steps:

i. providing the apparatus shown in FIG. 3 100;
ii. inserting transfusion blood through the first fluid inlet and subsequently passing said inserted transfusion blood through the first fluid conduit; and simultaneously 102, and simultaneously
iii. passing a second fluid through the second fluid inlet and subsequently through the second fluid conduit 104; and
iv. retrieving the transfusion blood from the first fluid outlet, the retrieved transfusion blood or packed red blood cells comprising a lower concentration of free haemoglobin than present in the inserted transfusion blood 106.

A suitable membrane for use with the present invention would include MicroPES available from 3M/Membrana. The membrane is available in both hollow fibre and flat sheet versions.

Optionally, in order to achieve very low concentrations of the undesired species, several apparatuses of the present invention may be used in series.

It will be appreciated that the above described embodiments are given by way of example only and that various modifications thereto may be made without departing from the scope of the invention as defined in the appended claims.

It will also be appreciated that, although the invention is described using (human) blood as the first fluid. The present invention could be employed for treating any type of cell-containing first fluid, wherein said fluid comprises one or more "contaminants" and thus the cells require "washing". Additional first fluid may, for example, include mammalian or reptilian blood, or cell culture medium, among others well-known in the art. The invention could also be employed to wash any type of biological cells, such as those that may be used during fermentation and other microbiological processes. In one example, cells cultured in a lab suffer build-up of toxic substances, which may include metabolites such as lactic acid, or a harmful secretome of proteins and non-protein components such as non-protein components, such as lipids, micro-RNA and messenger-RNA, in their cell culture media. Said media therefore requires regular changing to permit continued culture of the cells. Said toxic substances could optionally be transported out of said cell culture media using the present invention. In a further example, biological cells, such as yeast, may be used for production of industrially applicable substance or metabolite, such as an antibiotic. In the example case of antibiotic production, the concentration of antibiotic over time could become toxic to the antibiotic-producing cells and therefore require cell washing. The present invention can preferably be used to remove said antibiotic and/or other toxic substance from the surrounding media. In examples using yeast, depending on the strain, yeast cells may be 3.0 μm to 4.0 μm in size up to 30.0 μm to 40.0 μm in size. For treating cells of differing sizes membranes of differing pore size may be needed.

The present invention may be further understood with reference to the following paragraphs:

A red blood cell washing apparatus arranged to exchange a contaminated first fluid containing red blood cells with an uncontaminated second fluid such that the red blood cells are now contained in an uncontaminated fluid, the apparatus comprising,
- a first fluid conduit and a second fluid conduit, the second fluid conduit being separated from the first fluid conduit by a semi-permeable membrane disposed therebetween;
- the first fluid conduit having a first fluid inlet and a first fluid outlet, the first fluid conduit arranged to transport the first fluid in a first direction between the first fluid inlet and the first fluid outlet;
- the second fluid conduit being arranged to house a second fluid;
- wherein the semi-permeable membrane comprises a plurality of pores arranged to permit transport of said one or more exchangeable entities from the first fluid to the second fluid;
- wherein the contaminated first fluid diffuses through the membrane and may be replaced with uncontaminated second fluid that counter-diffuses through the membrane. The first fluid may be SAGM or other solution used to suspend red blood cells in packed cells. The second fluid may be SAGM or other solution used in making up packed cells as widely used for blood transfusion and may contain desirable species.

A red blood cell washing apparatus arranged to separate blood cells from whole blood to produce packed cells and a separate blood plasma stream. The whole blood consists of blood cells suspended in blood plasma (first fluid) and the second fluid consists of SAGM or another solution suitable for constituting the liquid phase of whole blood. The apparatus comprises, a first fluid conduit and a second fluid conduit, the second fluid conduit being separated from the first fluid conduit by a semi-permeable membrane disposed therebetween;
- the first fluid conduit having a first fluid inlet and a first fluid outlet, the first fluid conduit arranged to transport the first fluid in a first direction between the first fluid inlet and the first fluid outlet;
- the second fluid conduit being arranged to house a second fluid;
- wherein the semi-permeable membrane comprises a plurality of pores arranged to permit transport of said one or more exchangeable entities from the first fluid to the second fluid; wherein the plasma from the whole blood diffuses through the membrane and may be replaced with second fluid that counter-diffuses through the membrane. The process may be conducted in more than one stage to separate red blood cells from white blood cells. The first fluid may be blood plasma (so that the mixture constitutes whole blood) or may be SAGM or other solution used to suspend red blood cells in packed cells.

The invention claimed is:

1. A red blood cell washing apparatus arranged to exchange one or more exchangeable entities in a cell-containing first fluid, the apparatus comprising:
    a first fluid conduit and a second fluid conduit, the second fluid conduit being separated from the first fluid conduit by a semi-permeable membrane disposed therebetween;
    the first fluid conduit having a first fluid inlet and a first fluid outlet, the first fluid conduit arranged to transport the first fluid in a first direction between the first fluid inlet and the first fluid outlet;
    the second fluid conduit being arranged to house a fixed volume of a stationary second fluid;
    wherein the semi-permeable membrane comprises a plurality of pores arranged to permit transport of the one or more exchangeable entities from the first fluid to the second fluid;
    wherein the one or more exchangeable entities comprise one or both of free hemoglobin and blood plasma; and
    wherein the first fluid is whole blood isolated from a human body, or packed red blood cells.

2. The cell washing apparatus as claimed in claim 1, wherein the apparatus is configured to allow the first direction to be changed.

3. The cell washing apparatus as claimed in claim 1, wherein the plurality of pores has a pore diameter, the pore diameter being selected from a range of 0.2 μm to 5.0 μm.

4. The cell washing apparatus as claimed claim 1, wherein the plurality of pores has a pore diameter, the pore diameter being selected from a range of 0.2 μm to 2.0 μm.

5. The cell washing apparatus as claimed claim 1, wherein the second fluid conduit extends through the first fluid conduit or the first fluid conduit extends through the second fluid conduit.

6. The cell washing apparatus as claimed claim 1, wherein one or both of the first fluid conduit and the second fluid conduit comprise a plurality of fluid channels.

7. The cell washing apparatus as claimed in claim 1, wherein the second fluid is an aqueous solution having a lower concentration of the one or more exchangeable entities than the first fluid.

8. The cell washing apparatus as claimed in claim 7, wherein the second fluid comprises a higher concentration of one or more beneficial species than the first fluid, the beneficial species being selected from a group consisting of glucose, adenine, mannitol, a salt, an amino acid, and a fungicide.

9. The cell washing apparatus as claimed in claim 8, wherein the second fluid comprises SAGM.

10. The cell washing apparatus as claimed in claim 1, wherein the first fluid is gravity fed.

11. The cell washing apparatus as claimed in claim 1, wherein the first fluid outlet comprises an aperture having a size, wherein the size is adjusted by a user.

12. The cell washing apparatus as claimed in claim 1, wherein the apparatus comprises at least one fluid pump, the at least one fluid pump arranged to pump the first fluid.

13. A cell washing apparatus arranged to exchange one or more exchangeable entities in a cell-containing first fluid, the apparatus comprising:

a first fluid conduit and a second fluid conduit, the second fluid conduit being separated from the first fluid conduit by a semi-permeable membrane disposed therebetween;

the first fluid conduit having a first fluid inlet and a first fluid outlet, the first fluid conduit arranged to transport the first fluid in a first direction between the first fluid inlet and the first fluid outlet;

the second fluid conduit being arranged to house a fixed volume of a stationary second fluid;

wherein the semi-permeable membrane comprises a plurality of pores arranged to permit transport of the one or more exchangeable entities between the first fluid and the second fluid, wherein the one or more exchangeable entities comprises at least one of free hemoglobin, free heme, free iron, blood plasma, potassium ions, or lactic acid.

14. A method of conditioning stored transfusion blood or stored packed red blood cells, the method comprising the steps of:

[i.] providing a cell washing apparatus, the apparatus comprising:

a first fluid conduit and a second fluid conduit, the second fluid conduit being separated from the first fluid conduit by a semi-permeable membrane disposed therebetween;

the first fluid conduit having a first fluid inlet and a first fluid outlet, the first fluid conduit arranged to transport the first fluid in a first direction between the first fluid inlet and the first fluid outlet;

the second fluid conduit being arranged to house a fixed volume of a second fluid;

wherein the semi-permeable membrane comprises a plurality of pores arranged to permit transport of one or more exchangeable entities from the first fluid to the second fluid, wherein the one or more exchangeable entities comprise one or both of free hemoglobin and blood plasma, and wherein the first fluid is transfusion blood isolated from a human body, or packed red blood cells;

[ii.] inserting the transfusion blood or packed red blood cells through the first fluid inlet and subsequently passing said inserted transfusion blood or packed red blood cells through the first fluid conduit; and simultaneously,

[iii.] providing a stationary second fluid in the second fluid conduit; and

[iv.] retrieving the transfusion blood or packed red blood cells from the first fluid outlet, the retrieved transfusion blood or packed red blood cells comprising a lower concentration of free hemoglobin and other contaminants than present in the inserted transfusion blood or packed red blood cells from step [ii.].

15. A method of washing cells, the method comprising the steps of:

[i.] providing a cell washing apparatus, the apparatus comprising:

a first fluid conduit and a second fluid conduit, the second fluid conduit being separated from the first fluid conduit by a semi-permeable membrane disposed therebetween;

the first fluid conduit having a first fluid inlet and a first fluid outlet, the first fluid conduit arranged to transport the first fluid in a first direction between the first fluid inlet and the first fluid outlet;

the second fluid conduit being arranged to house a fixed volume of a second fluid;

wherein the semi-permeable membrane comprises a plurality of pores arranged to permit transport of one or more exchangeable entities from the first fluid to the second fluid, wherein the one or more exchangeable entities comprises at least one of free hemoglobin, free heme, free iron, blood plasma, potassium ions, or lactic acid;

[ii.] inserting a cell-containing first fluid through the first fluid inlet and subsequently passing said inserted cell-containing first fluid through the first fluid conduit; and simultaneously,

[iii.] providing a stationary second fluid in the second fluid conduit; and

[iv.] retrieving the cell-containing first fluid from the first fluid outlet, the retrieved cell-containing first fluid comprising a lower concentration of one or more exchangeable entities than present in the inserted cell-containing first fluid from step [ii.].

* * * * *